(12) United States Patent
Apte et al.

(10) Patent No.: US 11,634,703 B2
(45) Date of Patent: Apr. 25, 2023

(54) METHOD AND SYSTEM FOR HIGH-THROUGHPUT PARTICLE HANDLING BY USE OF MAGNETIC FIELDS AND DEVICE

(71) Applicant: PSOMAGEN, INC., Rockville, MD (US)

(72) Inventors: Zachary Apte, San Francisco, CA (US); Jessica Richman, San Francisco, CA (US); Daniel Almonacid, San Francisco, CA (US); Eduardo Morales, San Francisco, CA (US); Constance Norris, San Francisco, CA (US); Nicolas Ordenes, San Francisco, CA (US); Pamela Nieto, San Francisco, CA (US)

(73) Assignee: Psomagen, Inc., Rockville, MD (US)

( * ) Notice: Subject to any disclaimer, the term of this patent is extended or adjusted under 35 U.S.C. 154(b) by 165 days.

(21) Appl. No.: 16/760,939

(22) PCT Filed: Mar. 4, 2019

(86) PCT No.: PCT/US2019/020575
§ 371 (c)(1),
(2) Date: May 1, 2020

(87) PCT Pub. No.: WO2019/169395
PCT Pub. Date: Sep. 6, 2019

(65) Prior Publication Data
US 2020/0392481 A1 Dec. 17, 2020

Related U.S. Application Data

(60) Provisional application No. 62/671,410, filed on May 14, 2018, provisional application No. 62/645,091, (Continued)

(51) Int. Cl.
*C12N 15/10* (2006.01)
*G01N 35/00* (2006.01)

(52) U.S. Cl.
CPC ...... *C12N 15/1013* (2013.01); *B03C 2201/18* (2013.01); *B03C 2201/26* (2013.01)

(58) Field of Classification Search
CPC ............ C12N 15/1013; B03C 2201/18; B03C 2201/26; B03C 1/28; B03C 1/12;
(Continued)

(56) References Cited

U.S. PATENT DOCUMENTS 5,567,326 A * 10/1996 Ekenberg ............... B03C 1/286
436/526
6,409,925 B1 * 6/2002 Gombinsky ....... G01N 35/1072
436/526

(Continued)

FOREIGN PATENT DOCUMENTS

CN 105733941 A * 7/2016
CN 107287194 A * 10/2017

(Continued)

OTHER PUBLICATIONS

Extended European Search Report issued in corresponding European Patent Application No. 19761035.5 dated Nov. 5, 2021.
(Continued)

*Primary Examiner* — Gene O Crawford
*Assistant Examiner* — Muhammad Awais
(74) *Attorney, Agent, or Firm* — Morgan, Lewis & Bockius LLP

(57) ABSTRACT

Embodiments of the system and/or method can include and/or apply a magnetic device for facilitating a magnetic field for isolating the nucleic acid material from a sample, the magnetic device including a support component; and a set of magnetic pins attached to the support component and
(Continued)

movable with at least three degrees of freedom when attached to the support component, where the set of magnetic pins provide adaptability to shapes of sample compartments of a sample container.

18 Claims, 9 Drawing Sheets

Related U.S. Application Data filed on Mar. 19, 2018, provisional application No. 62/637,959, filed on Mar. 2, 2018.

(58) Field of Classification Search
CPC ............ G01N 35/0098; G01N 35/1011; B01L 2200/0657; B01L 2300/0829; B01L 2400/043; B01L 3/0289
USPC .......................................................... 536/25.4
See application file for complete search history.

(56) References Cited

U.S. PATENT DOCUMENTS

| | | | | |
|---|---|---|---|---|
| 6,592,819 B1 * | 7/2003 | Ogura | ................... | B01J 19/0046 422/50 |
| 8,268,264 B2 * | 9/2012 | Lenz | ....................... | B03C 1/288 422/68.1 |
| 2004/0026444 A1 * | 2/2004 | DeSilva | ................... | B01L 9/547 73/863.32 |
| 2004/0037748 A1 * | 2/2004 | Hasan | ................... | B01L 3/0244 436/180 |
| 2006/0269385 A1 * | 11/2006 | Zobel | ........................ | B03C 1/30 414/810 |
| 2007/0105214 A1 * | 5/2007 | Micklash, II | ...... | G01N 35/1074 435/286.2 |
| 2007/0178016 A1 * | 8/2007 | Jost | ....................... | G01N 35/109 422/400 |
| 2017/0267996 A1 * | 9/2017 | Talmer | ............... | G01N 35/0098 |

FOREIGN PATENT DOCUMENTS

| | | | |
|---|---|---|---|
| JP | 2006-329986 A1 | | 12/2006 |
| KR | 20150114873 A | * | 9/2014 |
| KR | 20160148201 A | * | 6/2015 |
| KR | 20170061815 A | * | 11/2015 |
| WO | 2000/060116 A1 | | 10/2000 |
| WO | 2011/157303 A1 | | 12/2011 |

OTHER PUBLICATIONS

International Search Report and Written Opinion issued in International Application No. PCT/US19/020575 dated May 17, 2019.
Office Action issued in corresponding Japanese Patent Application No. 2020-536003 dated Jan. 30, 2023 with English Translation.

* cited by examiner magnetic device 110 (MAGNETIC TOOL)

CONTACT INTERFACE 120 (OPTIONAL)

SUBSTANCE CONTAINER (RECIPIENT)

METHOD AND SYSTEM FOR HIGH-THROUGHPUT PARTICLE HANDLING BY USE OF MAGNETIC FIELDS AND DEVICE

CROSS-REFERENCE TO RELATED APPLICATIONS

This application is the U.S. National Phase under 35 U.S.C. § 371 of International Application No. PCT/US2019/020575 filed on Mar. 4, 2019, which claims the benefit of U.S. Provisional Application No. 62/637,959 filed on Mar. 2, 2018, U.S. Provisional Application No. 62/645,091 filed Mar. 19, 2018 and U.S. Provisional Application No. 62/671,410 filed May 14, 2018, which are each incorporated in their entirety herein by reference.

TECHNICAL FIELD

The disclosure generally relates to devices for sample processing, such as for experimental and diagnostic laboratories.

BACKGROUND

Nowadays, scientific technological developments have been increasingly applied to market products and solutions. Nonetheless, several barriers still exist for the transfer of scientific breakthroughs to concrete product developments. One of the obstacles that hinders the full development of these technologies is the significantly high cost and large amount of time for their productive processes, translating into less feasible options for large scale markets.

As part of the strategies to resolve these issues, laboratories have implemented an automated infrastructure to decrease expenses and time related to workforce, in a partial or complete mode. Additional factors that increases cost are materials and energetic resources. Thus, to accelerate the quantity and the variety of participation from this industry to market products, it is important to keep the focus on efficient and effective productive processes, that are able to reduce time and resources required for the scaling of scientific products. However, the complexity of some of the procedures required for the production and the high quality standards make result in a significant percentage of the processes not satisfying these requirements.

For instance, automated reagent handling platforms can conduct laboratory work, including handling of biological samples, nucleic acid and protein manipulation, solvent mixing, high-throughput sampling of small molecules, etc. Implementing these automated platforms allows entities to scale up the amount of samples processed, making the process highly reproducible while reducing the potential for sample contamination and minimizing the variability introduced by human-error, among other benefits.

The use of magnets can be applied for the mechanical-physical manipulation of particles attracted to magnetic fields (from hereon referred to as 'magnetic particles'), that can interact directly with chemical and biological materials of interest in a sample solution. Magnetic particles can be encapsulated with ionically charged polymers, or can be functionalized with specific chemical compounds to bind target molecules by ionic, hydrophobic or affinity interactions, among others. These magnetic particles can be captured by use of a magnet, and after removal of other substances from the container of interest by the use of manual or automated pipetting, and after one or more washing steps, only magnetic particles and their target bound molecules remain in the original container.

In automation contexts, magnets can be used as a base located underneath the recipient containing the solution to intervene. This magnetic base implies successive washing steps for the isolation of the particles from the rest of the solution, so it is obtaining a residual consequence of these cleanings. This implies a high expenditure of supplies for the washes and time.

Instead of handling the particles magnetically from the bottom, the particles can be handled from the surface, optionally mediated by a disposable intermediate between the tool and the solution, which can be performed in the context of manual manipulation.

The fit of the tool and the mediating element requires a closed high precision fit, thus restricting to model and brand compatibility to use with the tool.

Considering that these mediating elements are disposable, since their objective is to avoid contamination, the processes and raw material used for their manufacture are not of high precision or quality, there being a great variation of thickness and even shape between the same elements of the same batch manufactured. This physical incongruence could damage the performance of the process since it is based on the quality of the fit of the elements, in addition to restricting the brand and models of mediating elements, which could be a risk of obsolescence and cost.

Manipulation of nucleic acids can be performed with ionically charged magnetic beads. This process can include mixing the magnetic beads with the sample of interest in the presence of an ionic solution. Next, the mixture is incubated for a defined amount of time to allow the nucleic acids to bind the magnetic beads, followed by moving the plate or tube containing the sample to a surface that contains a magnet (e.g., either for a single tube or a magnetic plate). The magnetic field attracts the beads, and as a consequence the nucleic acids, to the side of the tube where they remain attached. Following, samples are washed a variable number of times during which the beads remain attached to the side of the container where the magnet is present, due to the magnetic field. Finally, beads are dried to remove residual liquids, removed from the magnetic plate, and water or any other suitable solution is added to release the nucleic acids from the beads, and the clean nucleic acids are then transferred to a clean reservoir (e.g., tube, plate, etc.). Certain portions of such approaches can be time consuming and expensive, thereby limiting the number of samples that can be processed, which can be a major hurdle in scaling up the production process. One of the most time consuming and expensive steps during magnetic particle manipulation is the use of disposable pipette tips, which have to be changed by the automation robot several times or by the operator if done manually, to avoid cross-contamination between reagents and samples, depending on the number of steps that are included in each pipeline. Furthermore, in order to handle varying volumes of liquids, pipette tips of different size must be used, requiring the change of the pipetting head tool at every single step, slowing down the process even further. The problem of extensive use of pipette tips and need to use pipette tips of different size are also encountered when samples are processed manually. Additionally, immobilization may occur to target magnetic particles in the automated workstation setup, and mobilization can sometimes be limited to when resuspended back to a liquid suspension and managed by liquid handlers, which can reduce the versatility of the platform.

DESCRIPTION OF THE EMBODIMENTS

The following description of the embodiments (e.g., including variations of embodiments, examples of embodiments, specific examples of embodiments, other suitable variants, etc.) is not intended to be limited to these embodiments, but rather to enable any person skilled in the art to make and use.

Figure 4:
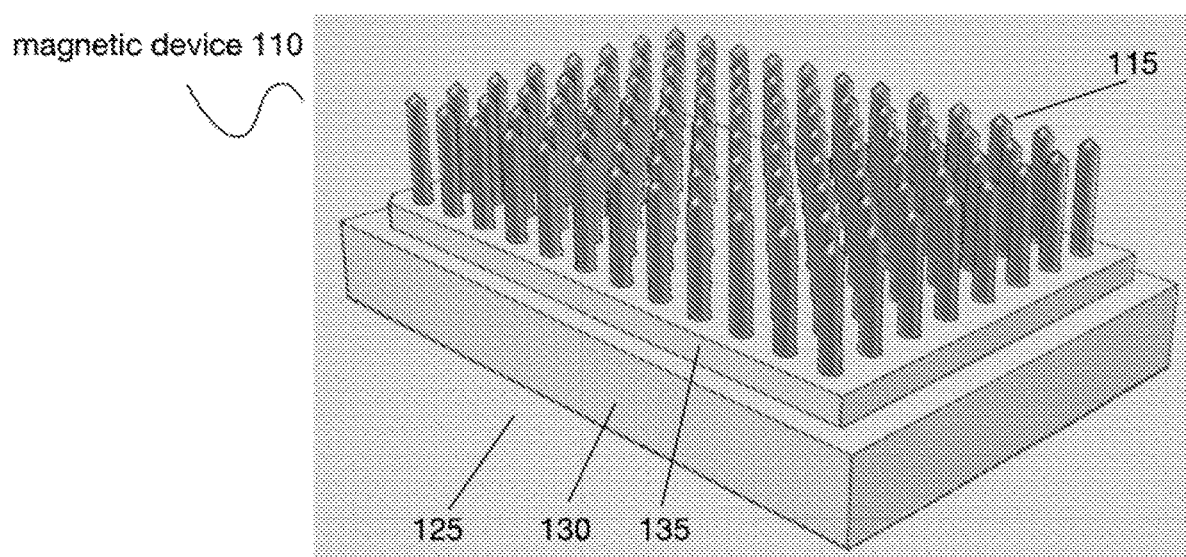
FIG. 4 includes a specific example of a frontal view visual representation of a magnetic device of an embodiment of the system.
Figure 5:
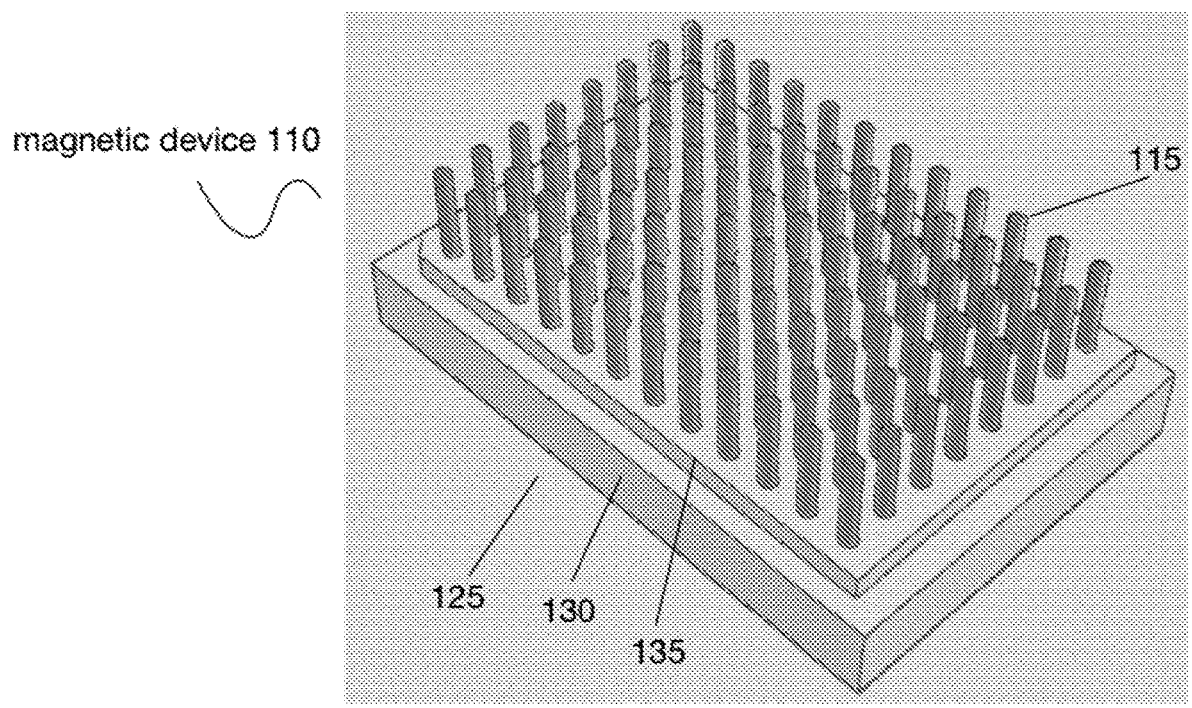
FIG. 5 includes a specific example of an upper view visual representation of a magnetic device of an embodiment of the system.
Figure 6:
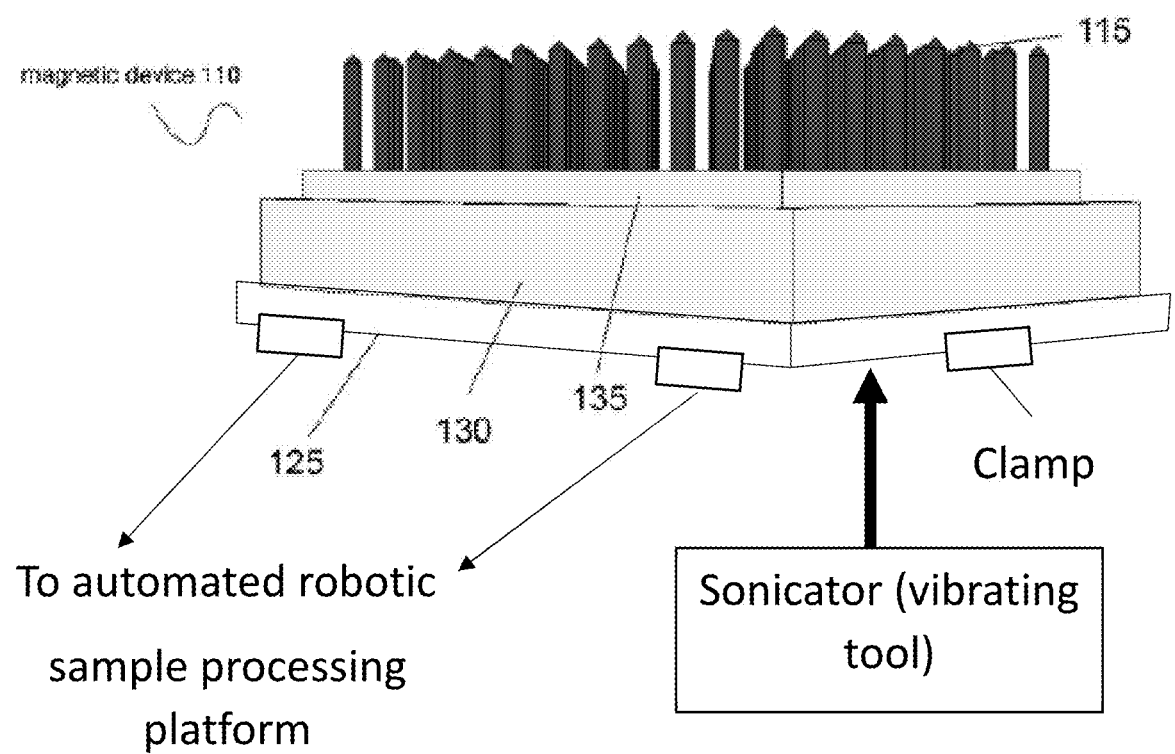
FIG. 6 includes a specific example of a lateral view visual representation of a magnetic device of an embodiment of the system.

As shown in FIG. 4-6, embodiments of a system 100 (e.g., for high-throughput particle handling; for isolating nucleic acid material, etc.) can include: a magnetic device no for facilitating a magnetic field for isolating the nucleic acid material from a sample, the magnetic device no including: a support component 125, and/or a set of magnetic pins 115 attached to the support component 125 and movable with at least three degrees of freedom when attached to the support component 125, wherein each pin of the set of magnetic pins 115 is independently movable from one another when attached to the support component 125, wherein the set of magnetic pins is configured to be inserted into at least one sample compartment housing the at least one sample, and/or wherein the independent movability of the set of magnetic pins 115 and the movability with the at least three degrees of freedom of the set of magnetic pins 115 provide adaptability to positions of magnetic beads attached with the nucleic acid material from the sample.

The support component can include one or more of: a lid 130 (e.g., a freely movable lid; movable manually by a manual operator; movable automatically by an automatic robotic sample processing platform; etc.) and a plate 135 attached to the freely movable lid and comprising a set of perforations, wherein each magnetic pin of the set of magnetic pins is mountable to each perforation of the set of perforations.

The magnetic device 110 can create a magnetic field for desired material (e.g., target elements; etc.) isolation (e.g., attract the material through magnetic means; etc.) and/or can transport desired material (e.g., where the magnetic device no can function as a transportation tool; etc.). The magnetic device preferably includes one or more magnetic pins 115 and/or suitable already magnetized components and/or components with potential to be magnetized by an additional action (e.g., direct or indirect actions, such as interactions with electromagnets; etc.). Such magnetic components can provide a dipole structure, either temporary or permanently. In specific examples, the force created by each dipole from the device can be powerful enough to attract and separate target element(s) of a substance (e.g., of a sample; etc.), and/or can exert a force of a magnitude enabling the fixing of the target element(s) to the magnetic pins 115 (and/or suitable magnetic component of the magnetic device no; etc.) and/or to a contact interface 120 between the magnetic pins 115 (and/or suitable magnetic component of the magnetic device no; etc.) and the target element(s) (e.g., between the magnetic pins 115 and the recipient container housing the target element(s), such as where the magnetic force and/or contact interface 120 can facilitate transportation of target elements without any risk of material detachment. Between the contact interface and the substance container there is a volumetric compatibility to facilitate the physical interaction between the objects which prioritizes maximizing contact surface between them, as shown in FIG. 2.

Figure 2:
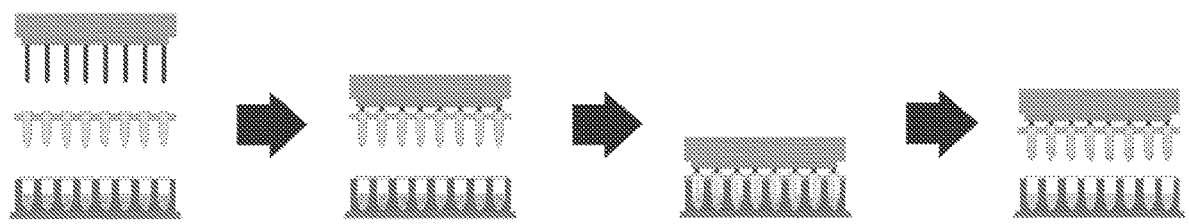
FIG. 2 includes a specific example of a visual representation of a functional workflow, in an embodiment of a method.

Embodiments of the method 200 can include (e.g., as shown in FIG. 2): inserting a set of magnetic pins of a magnetic device into at least one sample mixture comprising magnetic beads attached with nucleic acid material, wherein the set of magnetic pins is movable with at least three degrees of freedom when attached to a support component of the magnetic device, wherein each pin of the set of magnetic pins is independently movable from one another when attached to the support component, and/or wherein the independent movability of the set of magnetic pins and the movability with the at least three degrees of freedom of the set of magnetic pins provide adaptability to positions of the magnetic beads attached with the nucleic acid material.

Embodiments of the system 100 and/or method 200 can function to provide a fully automatable device and/or process for decreasing the cost and time for conducting automated handling of magnetic particles. In specific examples, magnetic particles of interest are directly pulled out of the working solution by the use of a magnetic field, making the process of magnetic particle handling independent of the use of pipette tips and changing of a pipetting head tool. In specific examples, embodiments of the system 100 can include one or more magnetic devices no that allow moving the attached magnetic particles through the desired work arrangement, resulting in a faster and more dynamic manipulation of the particles and their attached molecules (e.g., immobilized beads can be rapidly submerged sequentially in different liquid solutions, in a short time frame; etc.), reducing cost and the time required to complete the whole process (e.g., due to not requiring the use of pipette tips; etc.).

In specific examples, the system 100 and/or method 200 establish an operational methodology for the isolation of specific element(s) (e.g., constituents, etc.) of a substance by handling the element(s) through the application of magnetic principles, such as in an inverse dynamics of functioning with respect to nucleic acid extraction and/or other suitable approaches.

Embodiments of the system 100 and/or method 200 can additionally or alternatively be integrated with any suitable components, such as sample processing automation equipment (e.g., that occupies or includes a compression clamp and/or analogous component; etc.). In specific examples, the magnetic device no can be integrable (e.g., can be integrated, etc.) with one or more automated robotic sample processing platforms. Additionally or alternatively portions of embodiments of the system 100 and/or method 200 can be used by and or be performed manually by direct operator management.

Embodiments of the system 100 and/or method 200 can function to adapt to fit with other elements. Components (e.g., magnetic pins 115, etc.) of the magnetic device no can be movable with at least three independent (e.g., independent of each other, etc.) degrees of freedom (e.g., at least X, Y, and Z axes, etc.), which can allow the components (e.g., magnetic pins 115, etc.) to adapt to the different surfaces (e.g., ends of the surfaces; the interior faces; etc.) to which it can attach. In a specific example, each magnetic pin is independent of the other and has freedom of movement in 3 axes, including lineal position (X&Y axes) and depth (Z axis), which allows it to adapt to surface irregularities.

In specific examples, degrees of freedom of movement for the magnetic pins 115 can ensure the quality of the process where the device no is used, since each magnetic pin 115 (and/or suitable magnetic component) adapts to the position and other physical characteristics of the element (e.g., target nucleic acid material; other targets; etc.) that is intervening, allowing an execution without a real timing monitoring requirement and reproducibility capacity. Embodiments of the system 100 and/or method 200 can be used in an automation context, with no human operator, such as where physical characteristics as volume, material and shape can be adapted to be compatible with robot use. In specific examples, the magnetic pins 115 are otherwise independent of one another and removable, allowing them to be repaired and replaced in case of failure without obstructing the tool. In specific examples, the movability of the magnetic pins 115 allows the magnets to be adapted in quantity and configuration from 1 to 96 (and/or any suitable number) when the magnetic device no is used, being able to be customized to the requirements of the context. In a specific example, each pin of the set of magnetic pins 115 is removable from and re-attachable to the support component 125, for adapting configuration of the set of magnetic pins 115 to a set of different sample compartments comprising different numbers of sample wells.

In specific examples, embodiments of the system 100 and/or method 200 can confer improvements in relation to reproductible, consistency, automated, customizable, compatible to use by a range kind of supplies, and/or compatible to use by a range kind of robots.

Embodiments of the system 100 and/or method 200 can be compatible with, include components of, be applied with, and/or can otherwise be associated with disposable sample plates (e.g., well plates; etc.) of any suitable formats and/or any suitable sample containers. The disposable sample plates and/or sample containers are preferably constructed with polystyrene and/or any other suitable material that can act as an interface between the magnet components (e.g., magnetic pins 115) and the sample.

Embodiments of the system 100 and/or method 200 can be used for isolation of any suitable types of nucleic acid material (e.g., DNA, RNA, mRNA, cDNA, genomic DNA, microorganism nucleic acid material, etc.).

Embodiments of the system 100 and/or method 200 can be compatible with, include components of, be applied with, and/or can otherwise be associated with automated processes and/or manual processes for sample processing. Embodiments of the system 100 and/or method 200 can be applied for any suitable liquids, semisolids, solids, biological materials, organic materials, inorganic materials, and/or any suitable materials.

In variations, the system 100 and/or method 200 can be applied for and/or can include processes of biomolecule isolation (e.g., nucleic acid purification), nucleic acid cleaning, nucleic acid normalization, protein pull-down, protein purification, and/or carbohydrate, lipid, antibody and/or small molecule isolation (e.g., purification; etc.) as well as drugs, pharmaceuticals and/or any other compounds and/or macromolecules of interest. In variations, the system 100 and/or method 200 can be applied for and/or can include processes of purification, normalization, isolation and/or extraction, such as wherein the target micro and/or nanoparticles can be susceptible to the action of magnetic fields, such as through manipulation of micro and nanoparticles samples, such as through the handling of magnetic particles.

In a variation, in the processes for selection of specific elements from a substance by the use of magnetism, the operating logic can be based on fixing the desired element and the removal of its physical context to isolate it. In a specific example, in the case of DNA purification (and/or isolation of any suitable nucleic acids and/or molecules), magnetic beads can be used, to which the DNA is attracted and temporarily attached. In a specific example, subsequently and after applying a magnetic field with the use of a magnetic stand (and/or at any suitable time), the beads and therefore the DNA are anchored to the base of the container in which they are located; While the DNA and the beads are fixed to the recipient (e.g., sample container), fluids are dispensed and aspirated repeatedly (e.g., washing, etc.) with the purpose of eliminating other compounds that belonged to the original substance and that are not of interest or that could inhibit/affect downstream processes, resulting in the isolation of the fixed material.

In a variation, the system 100 and/or method 200 can be applied for and/or can include the isolation of the element(s) selected by the intervention with the desired material itself. Hence, instead of removing remaining components of the substance, we directly remove the desired material from it (e.g., as opposed to isolation of the compounds of interest as a residual result of a succession of operations that implicates use of external resources and time; etc.).

Figure 1:
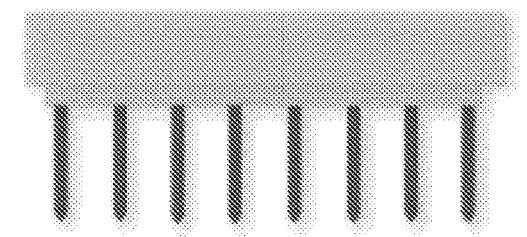
FIG. 1 includes a specific example of a visual representation of components of an embodiment of a system.
Figure 1:
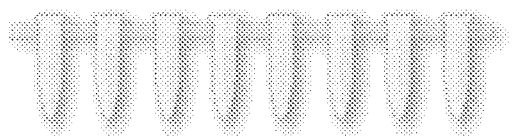
Figure 1:
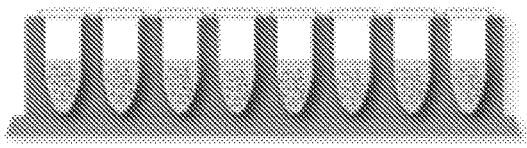

Additionally or alternatively to making the purification process faster, more effective, and efficient, as well as minimizing the use of other resources, variations of the system 100 and/or system 200 can allows the direct displacement of the desired material obtained because of the direct handling with the desired material (e.g., which can also help to decrease the quantity of materials required for other subsequent processes such as washing; as shown in FIG. 1; etc.).

In specific examples, the target material is fixed to a structure (e.g., magnetic pins 115) through magnetism, where the structure can be any means suitable to be magnetized, with or without the use of one or more intermediate contact interfaces 120 depending of the case, such as magnetic beads and/or physical interfaces such as plates between the structure and the substance, and/or any other suitable manner to achieve this purpose (e.g., as shown in FIG. 1). In a specific example, once the target material is fixed, it is separated and removed from the initial sample solution to isolate them from any other components present in the original container, and then can be taken directly to the next stages of the process. In a specific example, the target molecules are captured and retained in the original container and may or may not include the use of magnetic elements, and where the goal is to isolate a specific target material by retaining it, and after a series of consecutives washing steps, the material can be isolated and eluted into a solution without further contaminants and/or any other components.

In a specific example, the magnetic device 100 can be used in a non-automated experiment for the process of DNA extraction (and/or can be used for any suitable nucleic acid extraction, such as RNA extraction; etc.) from biological samples (e.g., biological samples including microorganisms, such as microorganism nucleic acid material; etc.). In a specific example, 96-well plates (e.g., 96-well polystyrene plates, etc.) are used, but any suitable plate with any suitable number of wells (e.g., other than 96; 6, 12, 24, 48 and/or 384-well plates; etc.) can additionally or alternatively be used. In a specific example, samples of interest in a 96-well polystyrene plate are mixed with ionically charged magnetic beads in an ionic solution and incubated briefly. In a specific example, new 96-well plate was fitted in the magnetic device no as a contact interface 120 (and/or any suitable sample container such as a well plate, and/or other suitable components can be used as a contact interface; etc.), and was placed into the plate containing the samples mixed with magnetic beads (e.g., where the wells of the contact interface 120 were placed into the openings of the wells of the plate holding the samples; etc.). In a specific example, after a brief incubation of the magnetic beads attached to the surface of the interface plate, the magnetics beads and the attached DNA are removed (e.g., by lifting the magnetic device no; etc.) from the samples. In a specific example, after removal of the magnetic beads with the attached DNA from the samples (and/or at any suitable time), the magnetic beads with the attached DNA are submerged in a new plate (e.g., new 96-well plate; etc.) holding a washing solution (e.g. ethanol 80%) for a suitable number of times (e.g., multiple times; once; etc.), further cleaning the nucleic acid molecules (e.g., the attached DNA; etc.). In a specific example, after cleaning (and/or at any suitable time), the magnetic beads with the attached DNA are submerged in water and/or any solvent able to detach the attached DNA (and/or suitable nucleic acid material) from the magnetic beads, thereby releasing the attached DNA (and/or suitable nucleic acid material). Released nucleic acid material (e.g., released nucleic acid material that was isolated from a sample using the magnetic device 110; etc.) can be used for any application (e.g., downstream application; etc.), including any one or more of: PCR, RT-PCR, library preparation, restriction enzyme analysis, ligation, and/or suitable applications.

In a specific example, as shown in Table 1, the DNA recovery yield can be evaluated when using any suitable portions of embodiments of the system 100 and/or method 200, where such DNA recovery yield can be quantified by a fluorescent dye assay. In a specific example, as shown in Table 1, the amount of DNA (ng/uL) recovered from ionically charged magnetic bead incubation of human samples, as measured with a fluorescent dye assay, where all samples were eluted from the beads in equal volumes of molecular grade water, hence, concentration is representative of the yield for each approach and allows a direct comparison; where a DNA-free sample lysis buffer was used as a negative control for the DNA extraction procedure; Mean values together with standard deviation values are indicated at the end of each column.

TABLE 1

| Human fecal Samples | Human Vaginal Samples | Negative Controls |
| --- | --- | --- |
| 3.25 | 3.29 | 0.0 |
| 8.12 | 16.88 | 0.0 |
| 31.33 | 17.08 | 0.0 |
| 5.81 | 18.72 | 0.0 |
| 10.73 | 8.53 | 0.0 |
| 25.11 | 16.91 | 0.00 ± 0.00 |
| 25.68 | 11.92 | |
| 2.93 | 9.20 | |
| 12.29 | 12.82 ± 5.47 | |
| 13.92 ± 10.69 | | |

Figure 3:
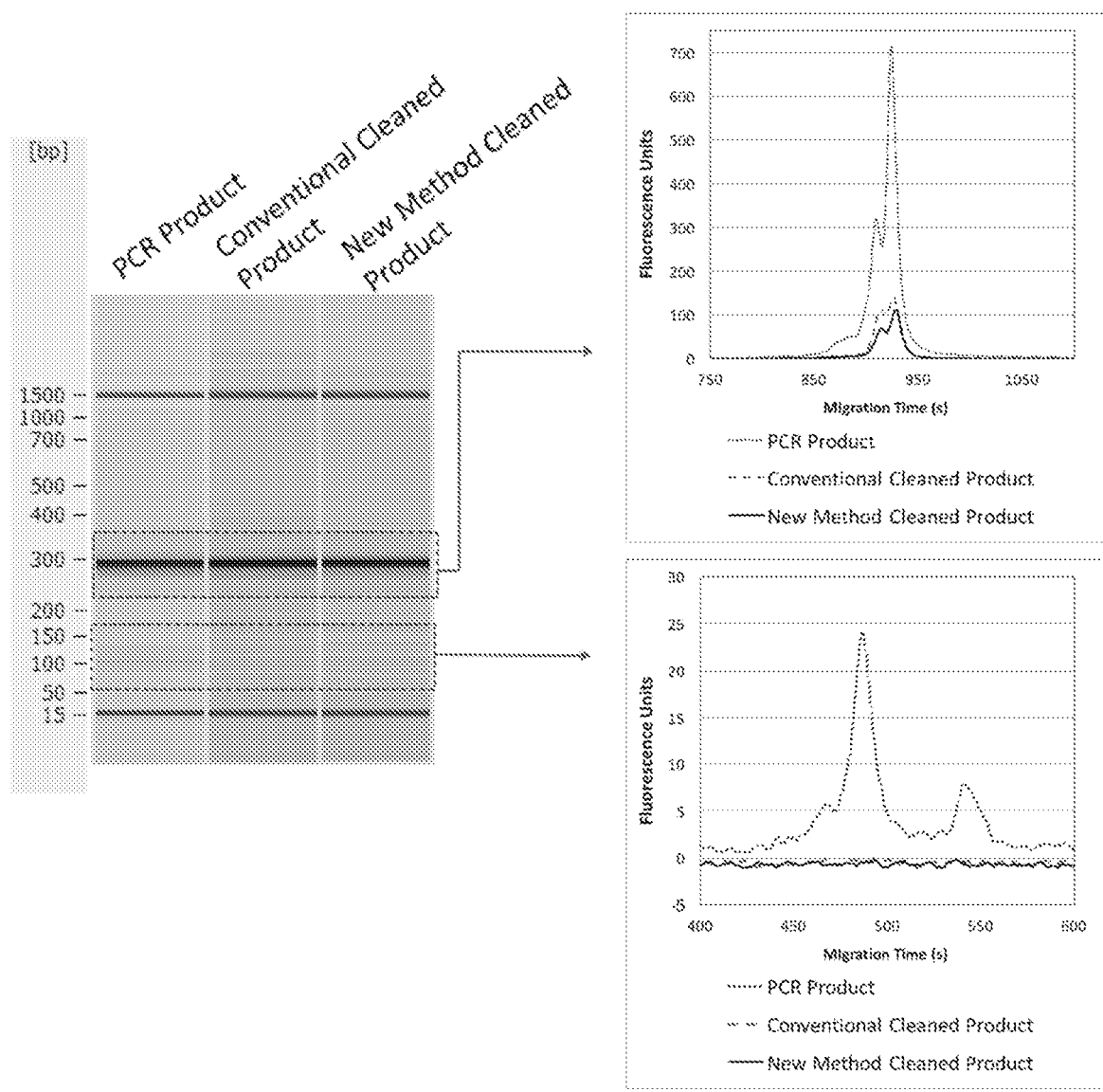
FIG. 3 includes a specific example of a comparison of DNA cleaning and purification from PCR reaction, where the DNA product of a PCR reaction was cleaned and purified with magnetic beads using a conventional magnet and compared against a magnetic device of an embodiment of a system; and where obtained DNA was analyzed by microfluidic electrophoresis, and where the purification yield for the band of interest (e.g., around 300 bp) is similar for the components being compared, and the ability to clean lower sized products (e.g., 100-150 bp) is similar for the components being compared.

In a specific example, DNA (and/or suitable nucleic acid material; such as microorganism nucleic acid material; genomic DNA; etc.) can be extracted, such as using one or more approaches described herein for purifying and cleaning DNA from products obtained from a PCR reaction. An objective of using magnetic beads for PCR product cleaning can include removing smaller sized DNA fragments (e.g., below 200 bp in length; below and/or in relation to any suitable size threshold; etc.) and other components of the PCR reaction while retaining target DNA molecules (e.g., bigger than 200 bp in length; above and/or in relation to any suitable size threshold; etc.). Any suitable portions of embodiments of the system 100 (e.g., the magnetic device no; etc.) and/or the method 200 can be applied to PCR cleanup (e.g., with magnetic beads; etc.), and, as shown in FIG. 3, can be compared to a conventional magnetic plate. In a specific example, as shown in FIG. 3, based on the fluorescence intensity of DNA in the PCR product, and the cleaned samples, the conventional magnet and the magnetic device no can purify similar yields of the DNA (and/or suitable nucleic acid material) of interest (e.g., band of approximately 300 bp); and where the ability to clean the sample from lower sized DNA products (e.g., of 100-150 bp in size) can be similar.

In variations, the method can include any combination of one or more of the following: add the beads and mix (manually or automatically) the solution containing the target to be extracted; incubate sufficient time to allow the targets to bind to the beads; take the magnetic device bound to the interface and sink it into the plate; incubate for between 0.5 and 10 minutes; take out the magnetic device with the beads attached on the exterior of the interface; the magnetic device is then sunk in a washing solution; incubate for between 0.5 and 10 minutes (optional); previous two steps can be repeated between 1 and 5 times; the magnetic device bound to the interface and beads is suspended between 0.5 and 15 minutes for the solvent to evaporate; the magnetic device bound to the interface and beads is sunk into a plate containing a solution to elute and release the target from the beads; the magnetic device is then removed and the interface is kept; incubate for between 0.5 and 5 minutes to ease the release of the target by hydrating it; use a vibrating or shaking device connected to the interface to ease the release of the target from the beads (optional); and/or the magnetic device is bound back to the interface to remove the remaining beads from the solution.

In specific examples, the method 200 can include incubating the set of magnetic pins in the at least one sample mixture for between 0.5 and 10 minutes; after removal of the set of magnetic pins from the at least one sample mixture, inserting the set of magnetic pins into at least one of a washing solution and an elution solution; after inserting the set of magnetic pins into the at least one of the washing solution and the elution solution, using a vibrating device to release the magnetic beads from the set of magnetic pins; and/or wherein the set of magnetic pins is housed in a set of contact interfaces providing a first intermediary between the set of magnetic pins and the sample mixture, a second intermediary between the set of magnetic pins and the at least one of the washing solution and the elution solution.

In specific examples, the independent movability of the set of magnetic pins and the movability with the at least three degrees of freedom of the set of magnetic pins facilitate direct attraction of magnetic beads attached with the nucleic acid material, without intervening surfaces between the set of magnetic pins and the directly attracted magnetic beads attached with the nucleic acid material. In specific examples the at least three degrees of freedom comprise a first degree of freedom in x-axis, a second degree of freedom in y-axis, and a third degree of freedom in z-axis.

In specific examples, the method 200 can include before inserting the set of magnetic pins of into the at least one sample mixture, integrating the magnetic device with an automated robotic sample processing platform. In specific examples, integrating the magnetic device comprises integrating the magnetic device via a compression grip component of the magnetic device, wherein the compression grip component comprises at least one of: a tong, a clamp, and a fastener.

Figure 7:
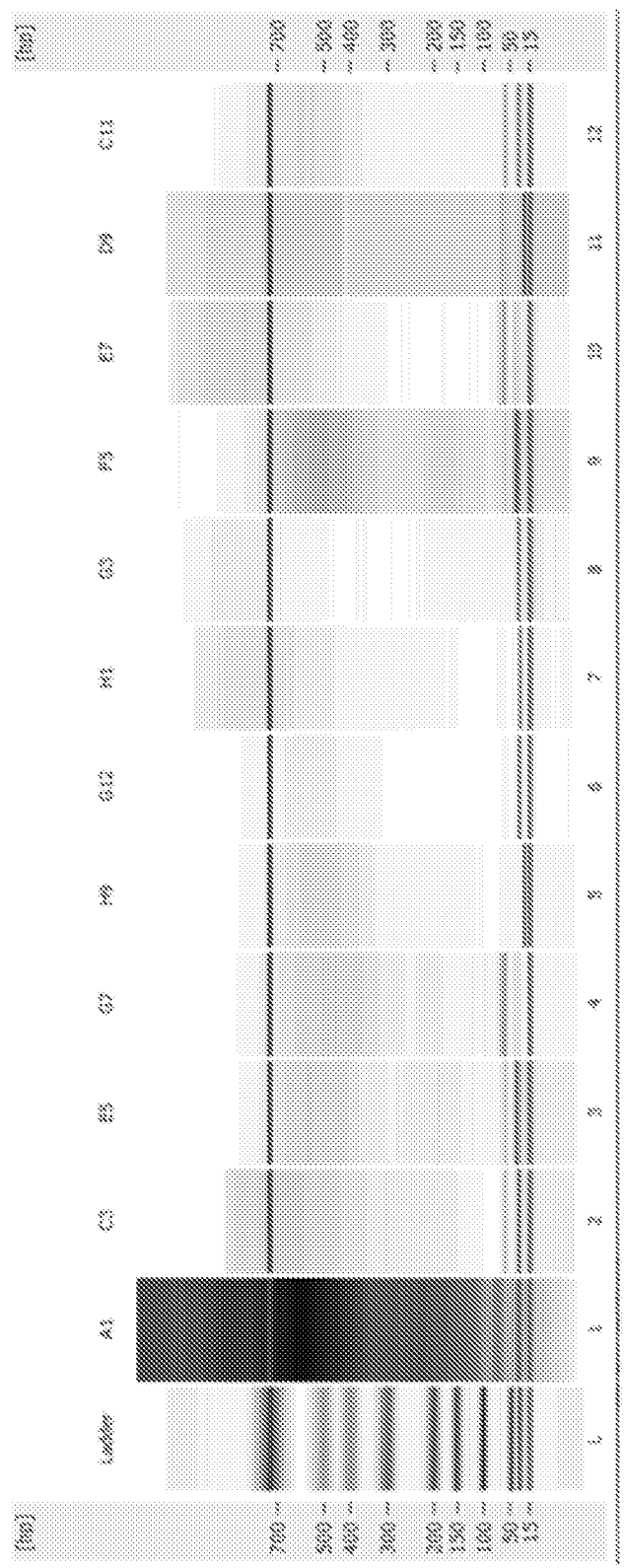
FIG. 7 includes a specific example of sizes of fragments of libraries obtained.

In variations, the system 100 and/or method 200 can be applied for metagenomic library construction (e.g., for microorganism metagenome sequencing library preparation for metagenomic sequencing; etc.). In a specific example, after PCR (e.g., with P5/P7 sequencing adapters; etc.) and before DNA normalization, (and/or at any suitable time), a magnetic device no can be applied with magnetic beads (e.g., for attaching target nucleic acid material; etc.), and results can be visualized (e.g., with bioanalyzer to evaluate obtainment of samples with expected fragments, such as near 500 bp length), as shown in FIG. 7. In a specific example, as shown in FIG. 7, libraries can be obtained with different concentrations and similar sizes, which is visualized by different band intensities and sizes near of ~500 bp. In a specific example, index sequences and adapters sequences can be added to tagmented samples fragments (and/or suitable components) by PCR (and/or other suitable approaches).

Figures 8A, 8B:
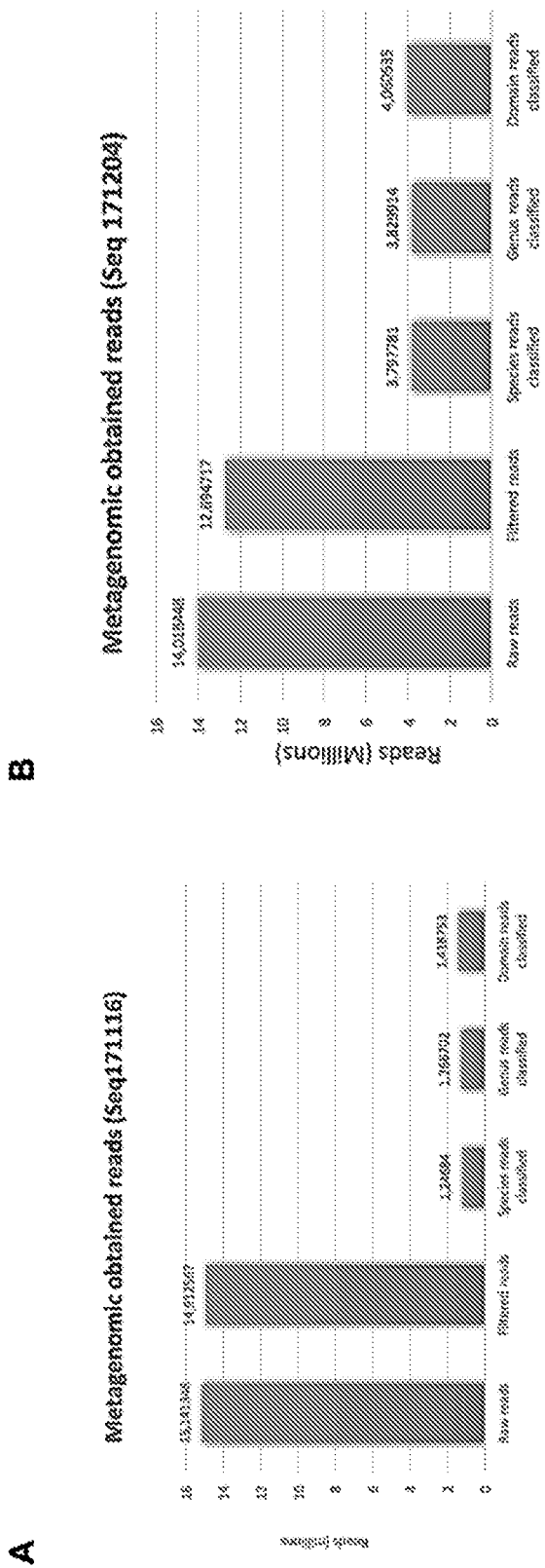
FIGS. 8A-8B include specific examples of metagenomic sequencing read results.

In variations, the system 100 and/or method 200 can be applied for metagenomic sequencing (e.g., using metagenomic libraries constructed using approaches described herein; etc.). In a specific example, two different metagenomic libraries were constructed, using gut and genital samples (e.g., gut-associated samples including microorganism nucleic acid material; genital samples including microorganism nucleic acid material; however any suitable samples associated with any suitable body sites can be additionally or alternatively be used in relation to any suitable approaches described herein; such as where body sites can include any one or more of gut sites, genital sites such as vaginal sites, mouth sites, nose sites, skin sites, etc.). In a specific example, each metagenomic library can be loaded with a 16S library constructed with a suitable pipeline, such as for evaluating metagenomic read amount and depth (e.g., in relation to functional and/or virulence genes; etc.). In specific examples, as shown in FIGS. 8A-8B: an average of 15M of total raw reads for both sequencing runs and 13M of passing filter reads; for seqrun 17.11.16, an average of 1.2 M of assigned reads per species, genus and domain were obtained; for seqrun 17.1204 an average of 4M of assigned read for the same taxonomic classification were obtained; more taxonomic assigned reads for seqrun 17.1204 were obtained compared to seqrun 17.11.16, which can indicate that use of a bead based normalization protocol (e.g., using the magnetic device 110) using a 1:20 of beads:PEG ratio per well can result in additional DNA yield recovery after water-based DNA elution step, which can be correlated with more assigned reads in the last sequencing run.

Figures 9A, 9B:
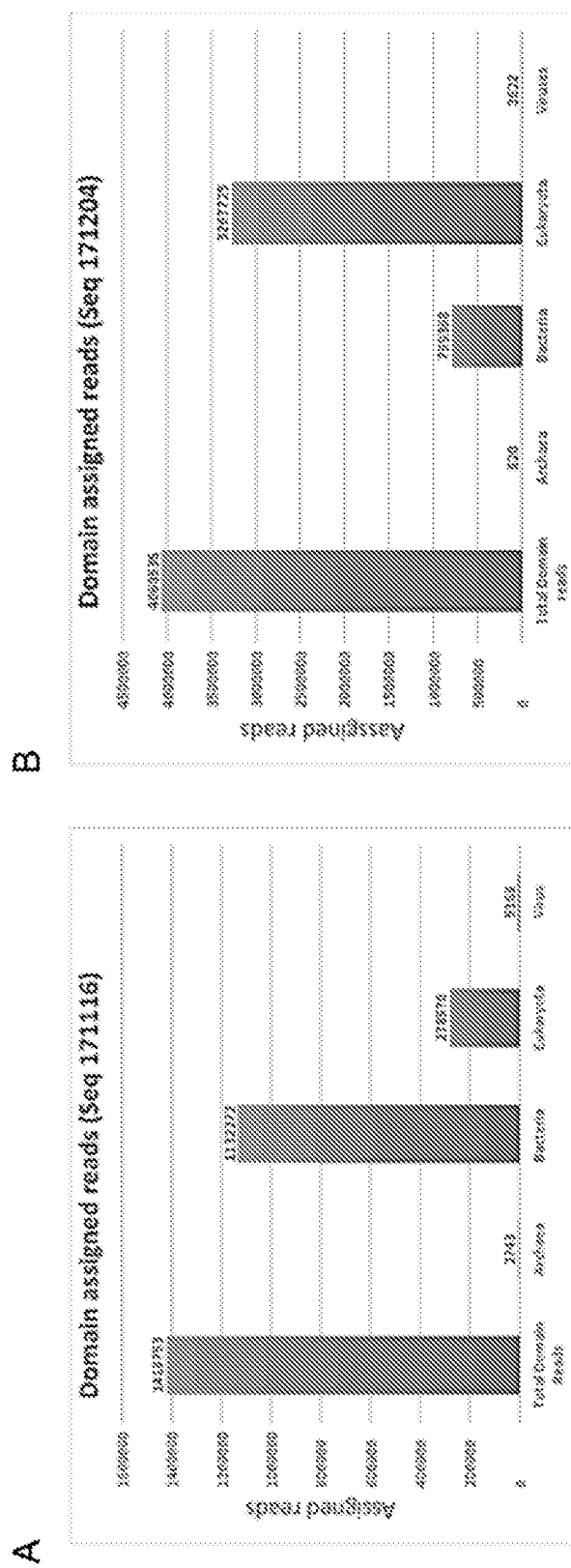
FIGS. 9A-9B include specific examples of metagenomic sequencing read results.

In specific examples, as shown in FIGS. 9A-9B, the sequencing run domain assigned reads data were subclassified in those assigned to Archaea, Bacteria, Eukarya and Viruses; both seq-runs included detection of viral and eukaryotic sequences; for Seqrun 17.11.16 ~1.2 M of bacteria assigned reads were obtained, while by bioinformatic analysis were assigned ~300.000 reads to eukaryotic domain (e.g., as shown in FIG. 9A); for Seq run 17.12.04, ~3M and ~800.000 reads were obtained for eukaryotic and bacteria respectively (e.g., as shown in FIG. 9B); where the difference in results may be explained by difference in bead normalization protocol, where for the bead and PEG ratio both libraries were constructed using 1:40 and 1:20 with bead:PEG buffer ratio; where 3M and ~260.000 Homo sapiens and pan troglodytes sequences reads for seqrun 17.12.04 and 17.11.16 were obtained, respectively, which can indicate that if using different bead:PEG ratios, the proportion of Homo sapiens and pan troglodytes sequences may be similar, therefore different bead ratios during bead normalization can have more input DNA to construct and consolidate the library.

In specific examples, the system 100 and/or method 200 can include and/or perform an automated metagenomic library construction pipeline (e.g., based on metagenomic libraries size obtained near of ~500 bp; etc.), where such approaches can identify different Taxonomic Orders in real samples (e.g., Eukaryotes, Archaea, Bacteria and/or viruses; etc.), and/or where such approaches can detect viral and/or eukaryotic microorganism sequences from gut and/or genital samples.

Embodiments of the method 100 and/or system 200 can include every combination and permutation of the various system components and the various method processes, including any variants (e.g., embodiments, variations, examples, specific examples, figures, etc.), where portions of embodiments of the method 100 and/or processes described herein can be performed asynchronously (e.g., sequentially), concurrently (e.g., in parallel), or in any other suitable order by and/or using one or more instances, elements, components of, and/or other aspects of the system 200 and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the method 100 and/or system 200 can be embodied and/or implemented at least in part as a machine configured to receive a computer-readable medium storing computer-readable instructions. The instructions can be executed by computer-executable components that can be integrated with embodiments of the system 200. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the method 100, system 200, and/or variants without departing from the scope defined in the claims. Variants described herein not meant to be restrictive. Certain features included in the drawings may be exaggerated in size, and other features may be omitted for clarity and should not be restrictive. The figures are not necessarily to scale. Section titles herein are used for organizational convenience and are not meant to be restrictive. The description of any variant is not necessarily limited to any section of this specification.

We claim:

1. A system for isolating nucleic acid material, the system comprising:
    a magnetic device for facilitating a magnetic field for isolating the nucleic acid material from at least one sample, the magnetic device comprising:
    a support component; and
    a set of magnetic pins attached to the support component and movable with at least three degrees of freedom when attached to the support component,
    wherein each pin of the set of magnetic pins is independently movable from one another with at least three degrees of freedom,
    wherein the set of magnetic pins is configured to be inserted into at least one sample compartment housing the at least one sample to directly attract magnetic beads attached with the nucleic acid material from the at least one sample, without intervening surfaces between the set of magnetic pins and the directly attracted magnetic beads attached with the nucleic acid material.

2. The system of claim 1, wherein the magnetic device is integrable with an automated robotic sample processing platform.

3. The system of claim 2, wherein the magnetic device comprises a compression grip component for integration with the automated robotic sample processing platform, wherein the compression grip component comprises at least one of: a tong, a clamp, and a fastener.

4. The system of claim 1, wherein the magnetic device is attachable to a vibrating tool for facilitating release of the magnetic beads from the magnetic pins.

5. The system of claim 1, wherein the support component is movable for displacing the set of magnetic pins out of the sample compartments and into at least one of a washing solution and an elution solution.

6. The system of claim 1, wherein the set of magnetic pins is housed in a set of contact interfaces providing an intermediary between the set of magnetic pins and the sample when the set of magnetic pins is inserted into the sample compartments, wherein each contact interface houses at least one magnetic pin of the set of magnetic pins.

7. The system of claim 1, wherein the set of magnetic pins comprises 96 magnetic pins with facet and position adaptability in at least 3 axes.

8. The system of claim 1, wherein each pin of the set of magnetic pins is removable from and re-attachable to the support component, for adapting configuration of the set of magnetic pins to a set of different sample compartments comprising different numbers of sample wells.

9. The system of claim 1, wherein the support component comprises:
    a freely movable lid; and
    a plate attached to the freely movable lid and comprising a set of perforations, wherein each magnetic pin of the set of magnetic pins is mountable to each perforation of the set of perforations.

10. System of claim 1, wherein the at least three degrees of freedom comprise a first degree of freedom in x-axis, a second degree of freedom in y-axis, and a third degree of freedom in z-axis.

11. A method for isolating nucleic acid material, the method comprising:
    inserting a set of magnetic pins of a magnetic device into at least one sample mixture comprising magnetic beads attached with nucleic acid material such that the set of magnetic pins is inserted into sample compartments housing the at least one sample mixture to directly attract magnetic beads attached with the nucleic acid material from the at least one sample mixture, without intervening surfaces between the set of magnetic pins and the directly attracted magnetic beads attached with the nucleic acid material,
    wherein the set of magnetic pins is movable with at least three degrees of freedom when attached to a support component of the magnetic device, and
    wherein each pin of the set of magnetic pins is independently movable from one another with at least three degrees of freedom when attached to the support component.

12. The method of claim 11, further comprising incubating the set of magnetic pins in the at least one sample mixture for between 0.5 and 10 minutes.

13. The method of claim 12, further comprising, after removal of the set of magnetic pins from the at least one sample mixture, inserting the set of magnetic pins into at least one of a washing solution and an elution solution.

14. The method of claim 13, further comprising, after inserting the set of magnetic pins into the at least one of the washing solution and the elution solution, using a vibrating device to release the magnetic beads from the set of magnetic pins.

15. The method of claim 14, wherein the set of magnetic pins is housed in a set of contact interfaces providing a first intermediary between the set of magnetic pins and the sample mixture, a second intermediary between the set of magnetic pins and the at least one of the washing solution and the elution solution.

16. The method of claim 11, wherein the at least three degrees of freedom comprise a first degree of freedom in x-axis, a second degree of freedom in y-axis, and a third degree of freedom in z-axis.

17. The method of claim 11, further comprising, before inserting the set of magnetic pins of into the at least one sample mixture, integrating the magnetic device with an automated robotic sample processing platform.

18. The method of claim 11, wherein integrating the magnetic device comprises integrating the magnetic device via a compression grip component of the magnetic device, wherein the compression grip component comprises at least one of: a tong, a clamp, and a fastener.

* * * * *